(12) United States Patent
Dinnell et al.

(10) Patent No.: US 7,342,009 B2
(45) Date of Patent: Mar. 11, 2008

(54) CYCLIC SULFONAMIDES FOR INHIBITION OF GAMMA-SECRETASE

(75) Inventors: Kevin Dinnell, Much Hadham (GB); Timothy Harrison, Great Dunmow (GB); Alan John Nadin, Sawbridgeworth (GB); Andrew Pate Owens, Hungtingdon (GB); Duncan Edward Shaw, Bishops Stortford (GB); Brian John Williams, Great Dunmow (GB)

(73) Assignee: Merck & Co., Inc., Rahway, NJ (US)

( * ) Notice: Subject to any disclaimer, the term of this patent is extended or adjusted under 35 U.S.C. 154(b) by 508 days.

(21) Appl. No.: 10/845,833

(22) Filed: May 14, 2004

(65) Prior Publication Data

US 2004/0230054 A1 Nov. 18, 2004

(30) Foreign Application Priority Data

May 16, 2003 (GB) .................................. 0311341.2
Nov. 20, 2003 (GB) .................................. 0327055.0

(51) Int. Cl.
*A61K 31/5415* (2006.01)
*C07D 279/02* (2006.01)
(52) U.S. Cl. .................... 514/224.2; 544/47; 514/224.2
(58) Field of Classification Search ................. 544/47; 514/224.2
See application file for complete search history.

(56) References Cited

U.S. PATENT DOCUMENTS

2006/0281737 A1  12/2006  Dinnell

FOREIGN PATENT DOCUMENTS

| WO | WO 00/50391 | 8/2000 |
|---|---|---|
| WO | WO 01/70677 | 9/2001 |
| WO | WO 02/36555 | 5/2002 |
| WO | WO 02/081435 | 10/2002 |
| WO | WO-02/081435 | * 10/2002 |
| WO | WO 03/055850 | 7/2003 |
| WO | WO 2004/101538 | 11/2004 |

* cited by examiner

*Primary Examiner*—Kamal A. Saeed
*Assistant Examiner*—Janet L Coppins
(74) *Attorney, Agent, or Firm*—John C. Todaro; William Krovatin

(57) ABSTRACT

Compounds of formula I:

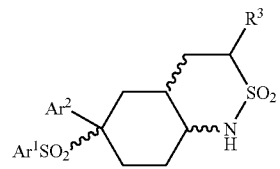

inhibit the processing of APP by gamma-secretase, and hence are useful in the treatment or prevention of Alzheimer's disease.

13 Claims, No Drawings

_US 7,342,009 B2_

CYCLIC SULFONAMIDES FOR INHIBITION OF GAMMA-SECRETASE

CROSS REFERENCE TO RELATED APPLICATIONS

This application claims priority under 35 U.S.C. § 119 from GB Application No. 0311341.2, filed May 16, 2003, and GB Application No. 0327055.0, filed Nov. 20, 2003.

The present invention relates to a novel class of compounds, their salts, pharmaceutical compositions comprising them, processes for making them and their use in therapy of the human body. In particular, the invention relates to novel cyclohexyl sulfones comprising an additional fused ring cyclic sulfonamide group. The compounds inhibit the processing of APP by γ-secretase so as to suppress or attenuate the secretion of β-amyloid, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There is a growing number of reports in the literature of compounds with inhibitory activity towards γ-secretase, as measured in cell-based assays (see, for example, WO 01/70677 and references therein). Many of the relevant compounds are peptides or peptide derivatives.

WO 00/50391 discloses a broad class of sulfonamides as modulators of the production of β-amyloid, but neither discloses nor suggests the compounds of the present invention. WO 01/70677, WO 02/36555 and WO 02/081435 disclose, respectively, classes of sulfonamides, sulfamides and cyclohexyl sulfones which inhibit γ-secretase, but neither disclose nor suggest the compounds of the present invention.

The present invention provides a novel class of cyclohexyl sulfones comprising an additional fused ring which contains a sulfonamide group. The compounds inhibit the processing of APP by the putative γ-secretase so as to suppress or attenuate the production of Aβ, and hence are useful in the treatment or prevention of AD.

According to the invention there is provided a compound of formula I:

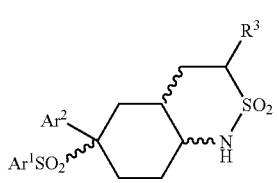

I wherein the bonds indicated by wavy lines are mutually cis with respect to the cyclohexane ring;

$R^3$ represents H or a hydrocarbon group of up to 10 carbon atoms, optionally substituted with $CF_3$, $CHF_2$, halogen, CN, $OR^5$, $COR^5$, $CO_2R^5$, $OCOR^6$, $N(R^5)_2$, $CON(R^5)_2$ or $NR^5COR^6$;

$R^5$ represents H or $C_{1-4}$alkyl;

$R^6$ represents $C_{1-4}$alkyl; and $Ar^1$ and $Ar^2$ independently represent phenyl or heteroaryl, either of which bears 0-3 substituents independently selected from halogen, CN, $NO_2$, $CF_3$, $CHF_2$, OH, $OCF_3$, CHO, CH=NOH, $C_{1-4}$alkoxy, $C_{1-4}$alkoxycarbonyl, $C_{2-6}$ acyl, $C_{2-6}$alkenyl and $C_{1-4}$alkyl which optionally bears a substituent selected from halogen, CN, $NO_2$, $CF_3$, OH and $C_{1-4}$alkoxy;

or a pharmaceutically acceptable salt thereof.

In formula I and other formulae presented herein a convention is used whereby wavy lines denote bonds which are mutually cis with respect to the cyclohexane ring. Such bonds either all project upwards from the ring or all project downwards from the ring. Sigma bonds attached to the cyclohexane ring and represented by a solid line necessarily have the opposite orientation to that of the bonds represented by wavy lines.

The compounds of formula I exist in two enantiomeric forms, depending on whether the bonds indicated by wavy lines project upwards or downwards, corresponding to formulae IA and IB:

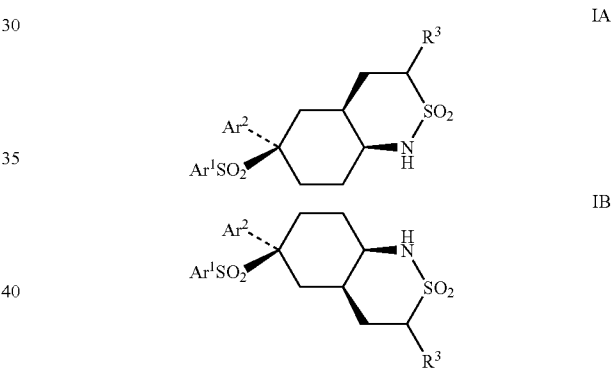

where $R^3$, $Ar^1$ and $Ar^2$ have the same meanings as before. It is to be understood that any compound in accordance with the invention may exist in either of the homochiral forms IA and IB, or as a mixture of the two in any proportion.

In addition to the isomerism described above, the compounds according to the invention may comprise one or more asymmetric centres, and accordingly may exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Where a variable occurs more than once in formula I, the individual occurrences are independent of each other, unless otherwise indicated. As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

As used herein, the expression "$C_{1-x}$ alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The expression "$C_{2-6}$ acyl" as used herein refers to $C_{1-5}$alkylcarbonyl groups in which the alkyl portion may be straight chain, branched or cyclic, and may be halogenated. Examples include acetyl, propionyl and trifluoroacetyl.

The expression "heteroaryl" as used herein means a monocyclic system of 5 or 6 ring atoms, or fused bicyclic system of up to 10 ring atoms, selected from C, N, O and S, wherein at least one of the constituent rings is aromatic and comprises at least one ring atom which is other than carbon. Monocyclic systems of 5 or 6 members are preferred. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of heteroaryl groups include tetrazole, 1,2,4-triazine and 1,3,5-triazine. Pyridine rings may be in the N-oxide form.

Where a phenyl group or heteroaryl group bears more than one substituent, preferably not more than one of said substituents is other than halogen or alkyl. Where an alkyl group bears more than one substituent, preferably not more than one of said substituents is other than halogen.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, benzenesulfonic acid, methanesulfonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

In the compounds of formula I, $Ar^1$ and $Ar^2$ independently represent optionally substituted phenyl or heteroaryl. $Ar^1$ is preferably selected from optionally substituted phenyl and optionally substituted 6-membered heteroaryl. Preferred 6-membered heteroaryl embodiments of $Ar^1$ include optionally substituted pyridyl, in particular optionally substituted 3-pyridyl. $Ar^1$ is preferably selected from 6-(trifluoromethyl)-3-pyridyl and phenyl which is optionally substituted in the 4-position with halogen, CN, vinyl, allyl, acetyl, methyl or mono-, di- or trifluoromethyl. In one preferred embodiment of the invention $Ar^1$ represents 4-chlorophenyl.

In another preferred embodiment $Ar^1$ represents 4-trifluoromethylphenyl. In another preferred embodiment $Ar^1$ represents 6-(trifluoromethyl)-3-pyridyl.

$Ar^2$ preferably represents optionally substituted phenyl, in particular phenyl bearing 2 or 3 substituents selected from halogen, CN, $CF_3$ and optionally-substituted alkyl. $Ar^2$ is typically selected from phenyl groups bearing halogen substituents (preferably fluorine) in the 2- and 5-positions, the 2- and 6-positions or in the 2-, 3- and 6-positions, or from phenyl groups bearing a fluorine substituent in the 2-position and halogen, CN, methyl or hydroxymethyl in the 5-position. In a preferred embodiment of the invention, $Ar^2$ represents 2,5-difluorophenyl, 2,6-difluorophenyl or 2,3,6-trifluorophenyl.

In a particular embodiment, $Ar^1$ is 4-chlorophenyl or 4-trifluoromethylphenyl and $Ar^2$ is 2,5-difluorophenyl.

$R^3$ represents H or a hydrocarbon group of up to 10 carbon atoms, optionally substituted as defined previously. Hydrocarbon groups represented by $R^3$ are preferably non-aromatic and unsubstituted, and preferably comprise up to 6 carbon atoms. Typical examples include alkyl groups (such as methyl, ethyl, n-propyl, isopropyl and n-butyl) and alkenyl groups (such as allyl).

Preferred compounds of the invention include those in which $Ar^1$ represents 4-chlorophenyl or 4-trifluoromethylphenyl, $Ar^2$ represents 2,5-difluorophenyl, and $R^3$ represents H, methyl, ethyl, n-propyl, isopropyl or allyl, and pharmaceutically acceptable salts thereof.

Specific examples of compounds in accordance with the invention include:

(4aRS,6RS,8aSR)-6-(2,5-difluorophenyl)-6-{[4-(trifluoromethyl)phenyl]sulfonyl}octahydro-1H-2,1-benzothiazine 2,2-dioxide;

(3S,4aR,6R,8aS)-6-(2,5-difluorophenyl)-3-ethyl-6-{[4-(trifluoromethyl)phenyl]sulfonyl}octahydro-1H-2,1-benzothiazine 2,2-dioxide;

(3R,4aR,6R,8aS)-6-(2,5-difluorophenyl)-3-ethyl-6-{[4-(trifluoromethyl)phenyl]sulfonyl}octahydro-1H-2,1-benzothiazine 2,2-dioxide;

(3RS,4aRS,6RS,8aSR)-6-(2,5-difluorophenyl)-3-isopropyl-6-{[4-(trifluoromethyl)phenyl]sulfonyl}octahydro-1H-2,1-benzothiazine 2,2-dioxide;

(3SR,4aRS,6RS,8aSR)-6-(2,5-difluorophenyl)-3-isopropyl-6-{[4-(trifluoromethyl)phenyl]sulfonyl}octahydro-1H-2,1-benzothiazine 2,2-dioxide; and (3S,4aR,6R,8aS)-6-[(4-chlorophenyl)sulfonyl]-6-(2,5-difluorophenyl)-3-ethyloctahydro-1H-2,1-benzothiazine 2,2-dioxide;

and the pharmaceutically acceptable salts thereof.

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula I or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's disease, a suitable dosage level is about 0.01 to 250 mg/kg per day, preferably about 0.05 to 100 mg/kg per day, more preferably about 0.1 to 50 mg/kg of body weight per day, and for the most preferred compounds, about 0.1 to 20 mg/kg of body weight per day. The compounds may be administered on a regimen of 1 to 4 times per day. In some cases, however, a dosage outside these limits may be used.

A preferred route to compounds of formula I in which $R^3$ is other than H comprises alkylation of compounds (1) with $R^{3a}$—L, followed by cleavage of the N-protecting group:

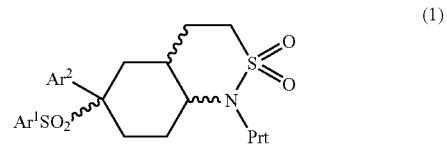

where $R^{3a}$ is $R^3$ that is other than H, L is a leaving group such as halide (especially bromide or iodide), mesylate, tosylate or triflate, Prt is a protecting group such as p-methoxybenzyl, and $Ar^1$ and $Ar^2$ have the same meanings as before. The alkylation takes place in an aprotic solvent (such as THF) in the presence of strong base (such as lithium bis(trimethylsilyl)amide) at reduced temperature (e.g. −78° C.). When Prt is p-methoxybenzyl, cleavage may be effected by treatment with acid, e.g. trifluoroacetic acid at ambient temperature in an inert solvent such as dichloromethane.

A preferred route to compounds (1) involves cyclisation of sulfonamides (2):

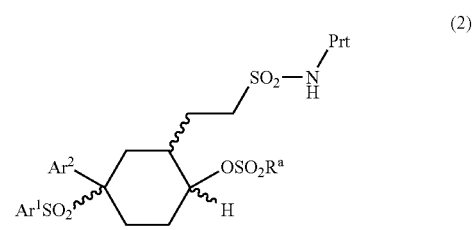

where $Ar^1$, $Ar^2$ and Prt have the same meanings as before, and $R^a$ represents $C_{1-6}$alkyl which optionally bears up to 3 halogen substituents (such as F or Cl), or phenyl which optionally bears up to 3 substituents selected from halogen and $C_{1-4}$alkyl. Examples of groups represented by $R^a$ include methyl, $CF_3$, phenyl, and p-tolyl, of which methyl is preferred. The cyclisation may be carried out by treatment with strong base such as sodium hydride in an aprotic solvent such as DMF at moderately elevated temperature (e.g. about 75° C.).

Compounds (2) are obtainable by reaction of sulfonyl chlorides (3) with $PrtNH_2$:

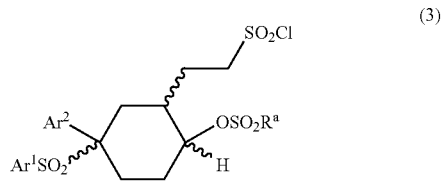

where $R^a$, $Ar^1$, $Ar^2$ and Prt have the same meanings as before. The reaction may be carried out in an inert solvent such as dichloromethane at about 0° C. using an excess of the amine.

Sulfonyl chlorides (3) are obtainable by reaction of sulfonates (4) with thiourea and treatment of the resulting adducts with chlorine:

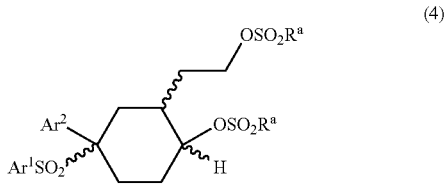
(4)

where $R^a$, $Ar^1$ and $Ar^2$ have the same meanings as before. The reaction with thiourea may be carried out in refluxing ethanol, and the resulting adduct may be treated with gaseous chlorine in aqueous acetic acid solution.

Sulfonates (4) are obtainable by treatment of diols (5) with $R^a SO_2 Cl$ or $(R^a SO_2)_2 O$:

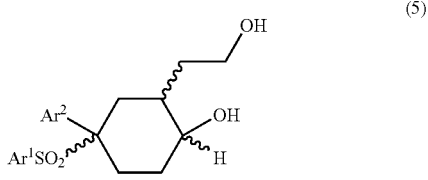
(5)

where $R^a$, $Ar^1$ and $Ar^2$ have the same meanings as before. The reaction is conveniently carried out in dichloromethane at about $-10°$ C. in the presence of a base such as triethylamine.

Diols (5) are obtainable by sequential treatment of ketones (6) with ozone and sodium borohydride:

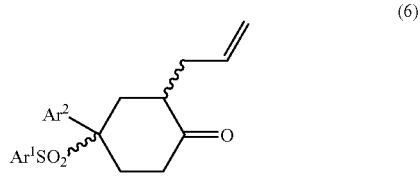
(6)

where $Ar^1$ and $Ar^2$ have the same meanings as before. The ozonolysis is typically carried out at about $-78°$ C. in a dichloromethane/methanol mixture, then sodium borohydride added with warming to ambient temperature.

Ketones (6) are obtained by alkylation of cyclohexanones (7) with allyl bromide or allyl iodide:

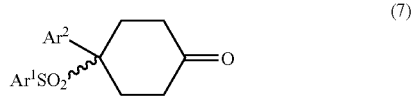
(7)

where $Ar^1$ and $Ar^2$ have the same meanings as before. The reaction may be carried out in THF at $-78°$ C. in the presence of strong base such as lithium hexamethyldisilazide. As an alternative to lithium hexamethyldisilazide, there may be employed the product obtained from reacting BuLi with a chiral amine such as [S-(R*,R*)]-(−)-bis(α-methylbenzyl)amine. This enables the isolation of compounds (6) in homochiral form, and hence the synthesis of homochiral compounds of formula I. The preparation of cyclohexanones (7) is described in WO 02/081435 and WO 04/013090.

Detailed procedures for this and other routes to the compounds of formula I are provided in the Examples section.

It will be apparent to those skilled in the art that individual compounds of formula I prepared by the above routes may be converted into other compounds in accordance with formula I by means of well known synthetic techniques such as alkylation, esterification, amide coupling, hydrolysis, coupling mediated by organometallic species, oxidation and reduction. Such techniques may likewise be carried out on precursors of the compounds of formula I. For example, substituents on the aromatic groups $Ar^1$ or $Ar^2$ may be added or interconverted by means of standard synthetic processes carried out on the compounds of formula I or their precursors. For example, a chlorine or bromine atom on $Ar^1$ or $Ar^2$ may be replaced by vinyl by treatment with vinyltributyltin in the presence of tri-t-butylphosphine, cesium fluoride and tris(dibenzylideneacetone)dipalladium(0). Ozonolysis of the vinyl group provides the corresponding formyl derivative, which may be transformed in a variety of ways, including oxidation to the corresponding acid, reduction to the corresponding benzyl alcohol, and conversion to the corresponding nitrile by treatment with hydroxylamine then triphenylphosphine and carbon tetrachloride.

Similarly, compounds of formula I in which $R^3$ is alkenyl such as allyl may be subjected to ozonolysis and further transformation in the manner described in the previous paragraph.

Where they are not themselves commercially available, the starting materials and reagents employed in the above-described synthetic schemes may be obtained by the application of standard techniques of organic synthesis to commercially available materials.

It will be appreciated that many of the above-described synthetic schemes may give rise to mixtures of stereoisomers. Such mixtures may be separated by conventional means such as fractional crystallisation and preparative chromatography.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallisation and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 3$^{rd}$ ed., 1999. The protecting groups may be removed at a convenient subsequent stage using methods known from the art.

An assay which can be used to determine the level of activity of compounds of the present invention is described in WO01/70677. A preferred assay to determine such activity is described in WO 03/093252.

Alternative assays are described in *Biochemistry*, 2000, 39(30), 8698-8704.

See also, *J Neuroscience Methods*, 2000, 102, 61-68.

The Examples of the present invention all had an $ED_{50}$ of less than 0.5 μM, typically less than 50 nM, in most cases less than 10 nM, and in preferred cases less than 1.0 nM, in at least one of the above assays.

The following examples illustrate the present invention. For the sake of convenience, compounds are depicted as being in accordance with formula IA even if they are racemic. Homochiral compounds are indicated by means of R and S configurational descriptors.

EXAMPLES

Intermediate 1

4-[(4-Chlorophenyl)sulfonyl]-4-(2,5-difluorophenyl)-2-[2-(trimethylsilyl)ethoxymethyl]cyclohexanone

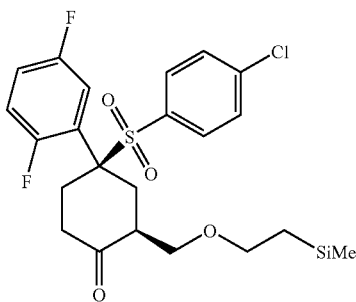

4-[(4-Chlorophenyl)sulfonyl]-4-(2,5-difluorophenyl)cyclohexanone (WO 02/081435) (2.0 g, 5.2 mmol) in dry tetrahydrofuran (10 mL) was added dropwise to a cooled solution of 0.5 M lithium hexamethyldisilazide in tetrahydrofuran (11.4 mL) at −78° C. The mixture was stirred at this temperature for 2 hours before adding 2-(trimethylsilyl)ethoxymethyl chloride (1.4 mL, 7.8 mmol) and the solution allowed to warm to rt. over 16 hours. The reaction mixture was diluted with ethyl acetate (10 mL), washed with water (10 mL), and the organic phase separated, dried (MgSO$_4$) and evaporated to dryness. The product was purified on silica eluting with [9:1] hexane-ethyl acetate to yield 1.2 g of the title compound. $^1$H NMR CDCl$_3$ 7.38 (4H, s), 7.24-7.16 (1H, m), 7.12-7.06 (1H, m), 6.97-6.87 (1H, m), 3.66 (1H, dd, J=9.7 and 3.0 Hz), 3.51-3.45 (3H, m), 3.17-3.15 (1H, m), 3.05-2.98 (1H, m), 2.56-2.49 (2H, m), 241-2.35 (2H, m), 2.23-2.17 (1H, m), 0.91-0.87 (2H, m) and 0.03 (9H, s).

Intermediate 2

4-[(4-Trifluoromethylphenyl)sulfonyl]-4-(2,5-difluorophenyl)-2-[2-(trimethylsilyl)ethoxymethyl]cyclohexanone

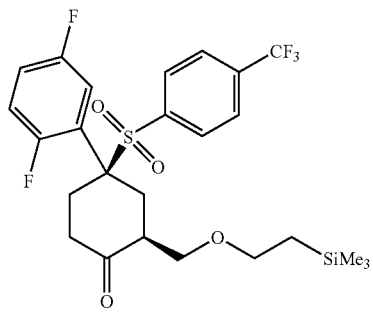

Prepared as for Intermediate 1, starting from 4-[(4-trifluoromethylphenyl)sulfonyl]-4-(2,5-difluorophenyl)cyclohexanone (WO 02/081435), and obtained as a solid. $^1$H NMR CDCl$_3$ 7.69-7.59 (4H, m), 7.24-7.18 (1H, m), 7.12-7.06 (1H, m), 6.93-6.86 (1H, m), 3.67 (1H, dd, J=9.7 and 2.9 Hz), 3.58-3.47 (3H, m), 3.20-3.16 (1H, m), 3.04-2.98 (1H, m), 2.57-2.51 (2H, m), 2.41-2.38 (2H, m), 2.24-2.16 (1H, m), 0.91-0.87 (2H, m) and 0.03 (9H, s).

Intermediate 3

(R,S)-4-[(4-Trifluoromethylphenyl)sulfonyl]-4-(2,5-difluorophenyl)-2-[2-(trimethylsilyl)ethoxymethyl]cyclohexanone

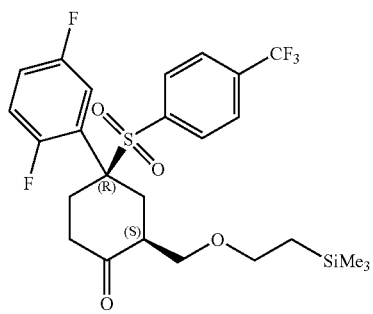

[(S-(R*,R*)]-(−)-Bis(α-methylbenzyl)amine (10 g, 44.4 mmol) and anhydrous lithium chloride (1.87 g, 44.5 mmol) were stirred in tetrahydrofuran (250 mL) under nitrogen gas, then cooled to −78° C. and treated slowly with butyllithium (1.6 mol solution in hexanes, 25.9 mL). The reaction mixture was allowed to warm up to 0° C. and stirred for 30 min. then re-cooled to an internal temperature of −100° C., stirring for 1 h. A solution of 4-[(4-trifluoromethylphenyl)sulfonyl]-4-(2,5-difluorophenyl)cyclohexanone (WO 02/081435) (12.5 g, 29.9 mmol) in tetrahydrofuran (50 mL), cooled to −78° C., was added slowly, maintaining the internal temperature at −100° C. The mixture was stirred at −100° C. for 2 h., then 2-(trimethylsilyl)ethoxymethyl chloride (7.9 mL, 44.7 mmol) was added, the resulting mixture warmed to −78° C., and allowed to warm up slowly overnight to −12° C. The reaction mixture was quenched with a 1M solution of citric acid then extracted with ethyl acetate. The organic extracts were washed with a 1M citric acid, 5% sodium bicarbonate solution, dried (MgSO$_4$), filtered and the solvent was removed. The resulting oil was purified by column chromatography on silica gel eluting with 2 to 10% ethyl acetate: isohexane to give the title compound as a clear oil. Yield 5 g (30%).

$^1$H NMR (400 MHz, CDCl$_3$) δ 7.69 (2H, d, J 8.4 Hz), 7.60 (2H, d, J 8.4 Hz), 7.23-7.18 (1H, m), 7.15-7.08 (1H, m), 6.96-6.86 (1H, m), 3.70-3.64 (1H, m), 3.53-3.48 (3H, m), 3.22-3.16 (1H, m), 3.08-2.98 (1H, m), 2.61-2.51 (2H, m), 2.43-2.36 (2H, m), 2.25-2.14 (1H, m), 0.94-0.83 (2H, m), 0.00 (9H, s). Chiral purity determined by chiral HPLC.

Intermediate 4 (R,S)

(R,S)-4-[(4-Chlorophenyl)sulfonyl]-4-(2,5-difluorophenyl)-2-[2-(trimethylsilyl)ethoxymethyl]cyclohexanone

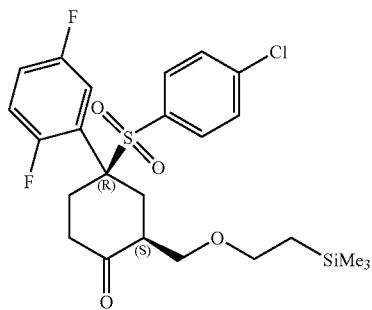

Prepared in the same manner as Intermediate 3 using the 4-[(4-chlorophenyl)sulfonyl]-4-(2,5-difluorophenyl)cyclohexanone as starting material. NMR data as for Intermediate 1.

Example 1

(4aRS,6RS,8aSR)-6-(2,5-difluorophenyl)-6-{[4-(trifluoromethyl)phenyl]sulfonyl}octahydro-1H-2,1-benzothiazine 2,2-dioxide

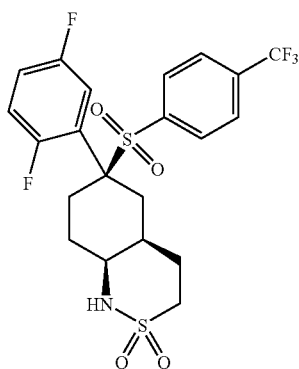

Step 1

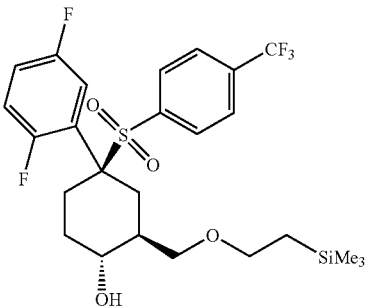

Intermediate 2 in isopropanol was treated with NaBH$_4$ (4 equiv.) at −40° C. and stirred whilst allowing to warm to rt. over 16 hours. The reaction was quenched with 8% aqueous citric acid, diluted with ethyl acetate, then the organic phase was separated, dried (MgSO$_4$) and evaporated to dryness. The trans product was purified on silica eluting with hexane-ethyl acetate mixtures.

Step 2

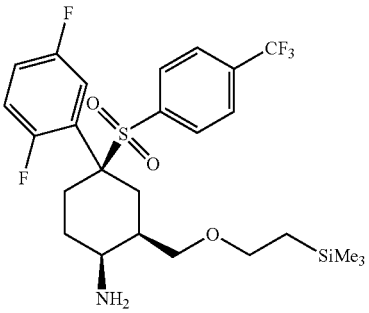

The alcohol from Step 1 in dichloromethane (100 mL) was treated with triethylamine (2 equiv.) at 0° C. and stirred whilst methanesulfonyl chloride (1.2 equiv.) was added. The reaction mixture was allowed to warm to r.t. over 1 hour, washed with water, 10% aqueous citric acid and saturated aqueous sodium hydrogen carbonate, then dried (MgSO$_4$) and evaporated to dryness. The residue was filtered through silica eluting with 20% ethyl acetate in hexanes to give the mesylate.

This solid in dimethylformamide was treated with sodium azide (approx. 2-fold excess) and heated to 95° C. for 8 hrs. The mixture was treated with water and extracted twice with ethyl acetate. The combined organics were washed with brine, dried (MgSO$_4$) and evaporated to dryness. The residue, in tetrahydrofuran and water (10:1 v/v), was treated with triphenylphosphine (1.2 equiv.) at room temperature for 15 mins and then the mixture was heated at reflux for 4 hrs. The mixture was allowed to cool to rt. and then passed through SCX Varian Bond Elut™ cartridge. The basic fraction was evaporated to give the primary amine. $^1$H NMR CDCl$_3$ 7.67-7.55 (4H, m), 7.09-7.00 (2H, m), 6.85-6.77 (1H, m), 3.51-3.16 (5H, m), 2.65-2.29 (4H, m), 1.76-1.71 (3H, m), 0.93-0.89 (2H, m) and 0.03 (9H, s).

MS MH$^+$ 550.

Step 3

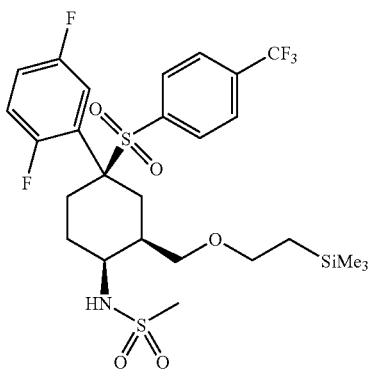

Triethylamine (175 μL, 1.26 mmol) was added to a solution of the product of Step 2 (230 mg, 0.419 mmol) and methanesulfonyl chloride (65 μL, 0.838 mmol) in dichloromethane (5 mL). The mixture was stirred at room temperature for 3 h., evaporated to dryness and the residue partitioned between ethyl acetate and 2 M hydrochloric acid. The organic layer was washed with 2 M hydrochloric acid, and then 4 M sodium hydroxide, dried (MgSO$_4$), filtered and the solvent removed to give the desired methanesulfonamide as a light yellow foam. Yield 263 mg. $^1$H NMR (400 MHz, CDCl$_3$) δ 7.64 (2H, d, J 8.3 Hz), 7.51 (2H, d, J 8.3 Hz), 7.05-7.02 (2H, m), 6.82-6.72 (1H, m), 5.66 (1H, brs), 3.69-3.66 (1H, m), 3.50-3.43 (4H, m), 2.96 (3H, s), 2.70-2.64 (1H, m), 2.55-2.42 (2H, m), 2.38-2.29 (1H, m), 2.19-2.11 (1H, m), 1.72-1.63 (1H, m), 1.40-1.31 (1H, m), 0.95-0.89 (2H, m), 0.00 (9H, s).

Step 4

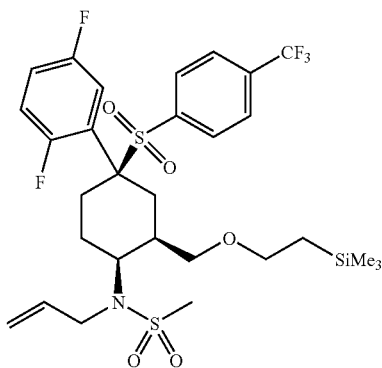

The product of Step 3 (263 mg, 0.419 mmol) in dimethylformamide (5 mL) was treated with sodium hydride (60% dispersion in mineral oil, 90 mg, 2.25 mmol), the mixture was stirred at room temperature for 30 min., then allyl bromide (382 μL, 4.51 mmol) was added, and the mixture heated to 65° C. and stirred overnight. The cooled mixture was quenched with water and extracted with ethyl acetate. The organic extract was washed with water, dried (MgSO$_4$), filtered and the solvent was removed. The residue was purified by column chromatography on silica gel eluting with 25% ethyl acetate:75% isohexane to give the N-allyl derivative as a yellow foam. Yield 150 mg.

$^1$H NMR (360 MHz, CDCl$_3$) δ 7.83 (2H, d, J 8.3 Hz), 7.72 (2H, d, J 8.3 Hz), 7.25-7.19 (2H, m), 7.04-6.97 (1H, m), 6.16-6.07 (1H, m), 5.59 (1H, d, J 17.4 Hz), 5.48 (1H, d, J 10.3 Hz), 4.39-4.22 (2H, m), 4.18-4.15 (1H, m), 3.78-3.73 (1H, m), 3.66-3.61 (2H, m), 3.53-3.48 (1H, m), 3.02 (3H, s), 2.94-2.90 (1H, m), 2.84-2.82 (2H, m), 2.63-2.55 (1H, m), 2.28-2.21 (1H, m), 2.10-2.04 (1H, m), 1.99-1.92 (1H, m), 1.09-1.02 (2H, m), 0.17 (9H, s).

Step 5

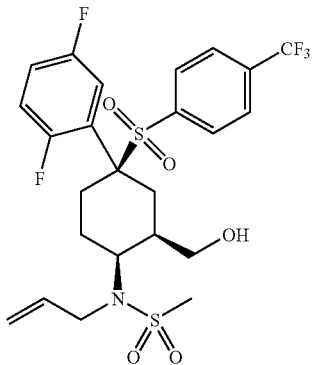

The product of Step 4 (150 mg, 0.225 mmol) in dichloromethane was treated with boron trifluoride diethyl etherate (250 μL, 1.99 mmol) and after 2 hours the mixture was cooled to 0° C. and stirred during the addition of sodium hydroxide (2.5M). The layers were separated and the organics were washed with brine, dried (MgSO$_4$) and evaporated to give an oil which was azeotroped with heptane to give the alcohol (115 mg).

$^1$H NMR (500 MHz, CDCl$_3$) δ 7.67 (2H, d, J 8.2 Hz), 7.53 (2H, d, J 8.2 Hz), 7.08-7.06 (2H, m), 7.11-7.05 (1H, m), 6.00-5.91 (1H, m), 5.49 (1H, d, J 17.2 Hz), 5.37 (1H, d, J 10.4 Hz), 4.31-4.25 (1H, m), 4.20-4.10 (1H, m), 4.06-4.02 (1H, m), 3.88-3.81 (1H, m), 3.47-3.41 (1H, m), 3.40-3.38 (1H, m), 2.88 (3H, s), 2.69-2.62 (1H, m), 2.55-2.46 (1H, m), 2.35-2.26 (1H, m), 2.13-2.06 (1H, m), 1.95-1.87 (1H, m), 1.85-1.75 (1H, m).

Step 6

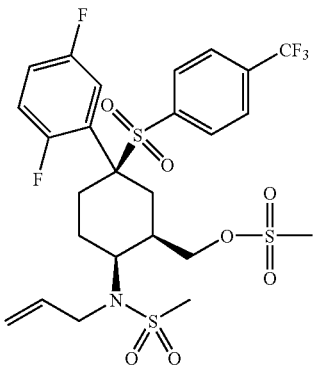

The alcohol from Step 5 (115 mg, 0, 203 mmol) and methanesulfonyl chloride (47 μL, 0.609 mmol) in dichloromethane (5 mL) were treated with triethylamine (141 μL, 1.01 mmol) and the mixture stirred at room temperature for 3 h. The solvent was removed under reduced pressure, and the residue partitioned between ethyl acetate and 2 M hydrochloric acid. The organics were collected, washed with 2 M hydrochloric acid, and then 4 M sodium hydroxide, dried (MgSO₄), filtered and the solvent was removed, azeotroping with toluene to remove all traces of ethyl acetate, to give the mesylate as a white foam. Yield 130 mg.

Step 7

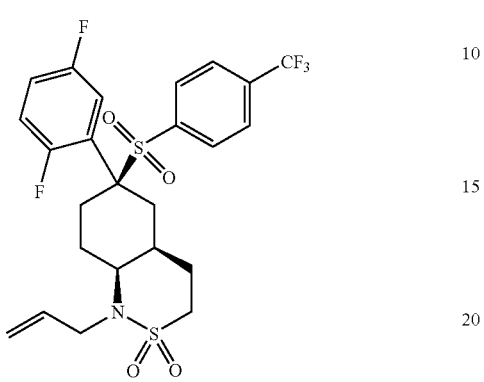

The mesylate from Step 6 (130 mg, 0.202 mmol) in tetrahydrofuran (5 mL) at −30° C. under nitrogen gas was treated with butyllithium (1.6 M solution in hexanes, 252 μL) and the reaction mixture was allowed to warm up slowly to room temperature, then quenched with water and extracted with ethyl acetate. The organic extract was washed with water, dried (MgSO₄), filtered and evaporated. The residue was purified by column chromatography on silica gel eluting with 25% ethyl acetate:75% isohexane to give the desired cyclic sulfonamide as a white powder. Yield 15 mg (14%).

¹H NMR (500 MHz, CDCl₃) δ 7.67 (2H, d, J 8.1 Hz), 7.53 (2H, d, J 8.1 Hz), 7.12-7.06 (2H, m), 6.88-6.77 (1H, m), 6.07-5.98 (1H, m), 5.28 (1H, dd, J 0.5 and 17.6 Hz), 5.23 (1H, dd, J 0.5 & 10.5 Hz), 4.41-4.31 (1H, m), 3.71-3.61 (1H, m), 3.28-3.20 (1H, m), 3.10-3.02 (1H, m), 2.91-2.80 (1H, m), 2.56-2.25 (5H, m), 1.98-1.90 (1H, m), 1.81-1.66 (1H, m), 1.45-1.30 (2H, m).

Step 8

The product of Step 7 (12 mg, 0.022 mmol) in toluene (2 mL) was treated with [1,3-bis(diphenylphosphino)propane]dichloronickel(II) (1.2 mg, 0.0022 mmol) then diisobutylaluminum hydride (1.5 M solution in toluene, 30 μL). The mixture was stirred at room temperature for 3 h., then quenched with 4 M sodium hydroxide and extracted with ethyl acetate. The organic extracts were dried (MgSO₄), filtered through a plug of silica gel eluting with ethyl acetate and evaporated to dryness. The residue was triturated in diethyl ether and the solid was collected to give the title compound as a white solid. Yield 6 mg (55%).

¹H NMR (500 MHz, CDCl₃) δ 7.67 (2H, d, J 8.1 Hz), 7.53 (2H, d, J 8.1 Hz), 7.12-7.07 (2H, m), 6.90-6.78 (1H, m), 4.45-4.37 (1H, m), 3.76-3.71 (1H, m), 3.20-3.11 (1H, m), 3.10-3.04 (1H, m), 2.71-2.61 (1H, m), 2.55-2.42 (2H, m), 2.40-2.29 (1H, m), 2.10-1.98 (1H, m), 1.91-1.84 (1H, m), 1.72-1.60 (2H, m), 0.98-0.91 (1H, m). m/z (ES⁻) (M−1) 508.

Example 2

(3S,4aR,6R,8aS)-6-(2,5-difluorophenyl)-3-ethyl-6-{[4-(trifluoromethyl)phenyl]sulfonyl}octahydro-1H-2,1-benzothiazine 2,2-dioxide

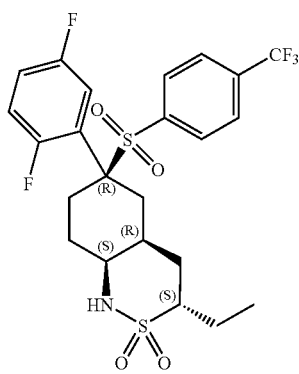

Step 1

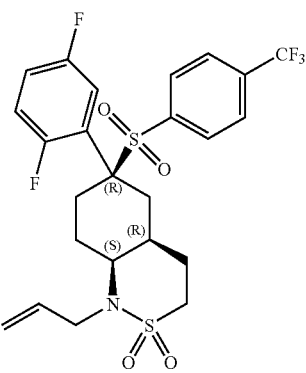

Intermediate 3 (830 mg, 1.29 mmol) was treated as described in Example 1 Steps 1-7 to give the chiral N-allyl sulfonamide as a white solid. Yield 300 mg (42%).

¹H NMR (500 MHz, CDCl₃) δ 7.67 (2H, d, J 8.1 Hz), 7.53 (2H, d, J 8.1 Hz), 7.12-7.06 (2H, m), 6.88-6.77 (1H, m), 6.07-5.98 (1H, m), 5.28 (1H, dd, J 0.5 and 17.6 Hz), 5.23 (1H, dd, J 0.5 and 10.5 Hz), 4.41-4.31 (1H, m), 3.71-3.61 (1H, m), 3.28-3.20 (1H, m), 3.10-3.02 (1H, m), 2.91-2.80 (1H, m), 2.56-2.25 (5H, m), 1.98-1.90 (1H, m), 1.81-1.66 (1H, m), 1.45-1.30 (2H, m).

Step 2

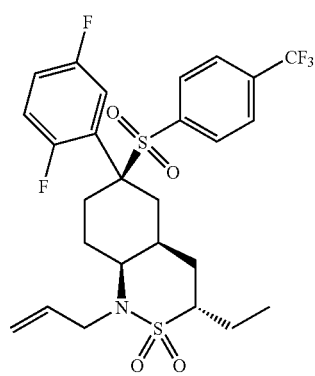

and

-continued

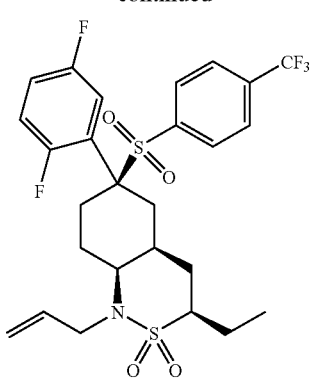

The product of Step 1 (80 mg, 0.146 mmol) in tetrahydrofuran (5 mL) at 0° C. was treated with lithium bis(trimethylsilyl)amide (1M solution in tetrahydrofuran, 292 μL) and the mixture was stirred at 0° C. for 30 min. before addition of iodoethane (15 μL, 0.188 mmol). The resulting mixture was allowed to warm up slowly overnight, quenched with water then extracted with ethyl acetate. The organic extracts were dried (MgSO$_4$), filtered and the solvent was removed. The residue was purified by column chromatography on silica gel eluting with 10 to 15% ethyl acetate:isohexane to give a less polar product (white solid, yield 28 mg, 33%):

$^1$H NMR (500 MHz, CD$_3$OH) δ7.81 (2H, d, J 8.3 Hz), 7.66 (2H, d, J 8.3 Hz), 7.24-7.15 (2H, m), 7.02-6.93 (1H, m), 6.04-5.93 (1H, m), 5.32 (1H, d, J 17.2 Hz), 5.19 (1H, d, J 10.1 Hz), 4.26 (1H, dd, J 5.1 & 17.2 Hz), 3.77 (1H, dd, J 7.0 & 17.2 Hz), 3.54 (1H, brs), 3.16-3.11 (1H, m), 2.83-2.68 (1H, m), 2.61-2.39 (2H, m), 2.33-2.02 (2H, m), 2.08-1.85 (2H, m), 1.55-1.28 (3H, m), 1.11-0.98 (3H, m), 0.93-0.82 (1H, m); and also a more polar product (white solid, yield 23 mg 27%):

$^1$H NMR (500 MHz, CD$_3$OH) δ 7.83 (2H, d, J 8.3 Hz), 7.66 (2H, d, J 8.3 Hz), 7.24-7.14 (2H, m), 7.04-6.94 (1H, m), 5.92-5.81 (1H, m), 5.24 (1H, dd, J 1.1 & 17.2 Hz), 5.13 (1H, dd, J 1.1 & 10.3 Hz), 4.13-4.05 (1H, dd, m), 3.75 (1H, dd, J 6.8 & 16.7 Hz), 3.59-3.53 (1H, m), 3.00-2.93 (1H, m), 2.70-2.55 (2H, m), 2.48-2.22 (4H, m), 2.13-2.03 (1H, m), 1.93-1.85 (1H, m), 1.75-1.66 (1H, m), 1.59-1.47 (1H, m), 1.17-1.07 (3H, m), 0.95-0.84 (1H, m).

Step 3

The less polar product from Step 2 (25 mg, 0.0433 mmol) was treated as described in Example 1 Step 8 to give the desired chiral sulfonamide as a white solid. Yield 20 mg (86%).

$^1$H NMR (500 MHz, CD$_3$OH) δ 7.82 (2H, d, J 8.2 Hz), 7.64 (2H, d, J 8.2 Hz), 7.23-7.08 (2H, m), 7.01-6.93 (1H, m), 3.57-3.52 (1H, m), 3.06-2.98 (1H, m), 2.75-2.56 (2H, m), 2.51-2.37 (2H, m), 2.00-1.91 (2H, m), 1.90-1.82 (1H, m), 1.74-1.55 (2H, m), 1.51-1.42 (1H, m), 1.23-1.20 (1H, m), 1.15-1.07 (3H, m), 0.97-0.84 (1H, m). m/z (ES$^-$) (M–1) 536.

Example 3

(3R,4aR,6R,8aS)-6-(2,5-difluorophenyl)-3-ethyl-6-{[4-(trifluoromethyl)phenyl]sulfonyl}octahydro-1H-2,1-benzothiazine 2,2-dioxide

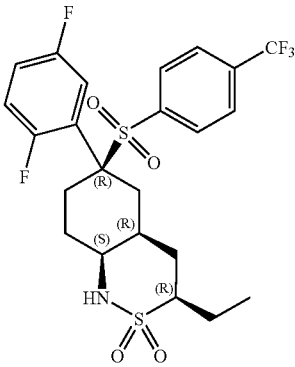

The more polar isomer from Example 2 Step 2 (23 mg, 0.0433 mmol) was treated as described in Example 1 Step 8 to give the desired chiral sulfonamide as a white solid. Yield 10 mg (46%).

$^1$H NMR (500 MHz, CD$_3$OH) δ 7.84 (2H, d, J 8.2 Hz), 7.65 (2H, d, J 8.2 Hz), 7.27-7.08 (2H, m), 7.04-6.94 (1H, m), 3.62-3.57 (1H, m), 2.93-2.86 (1H, m), 2.75-2.63 (1H, m), 2.56-2.49 (2H, m), 2.48-2.41 (1H, m), 2.40-2.32 (1H, m), 2.17-2.07 (1H, m), 2.00-1.93 (1H, m), 1.91-1.84 (1H, m), 1.79-1.70 (1H, m), 1.68-1.55 (1H, m), 1.32-1.25 (1H, m), 1.20-1.14 (3H, m), 0.98-0.85 (1H, m). m/z (ES$^-$) (M–1) 536.

Example 4

(3RS,4aRS,6RS,8aSR)-6-(2,5-difluorophenyl)-3-isopropyl-6-{[4-(trifluoromethyl)phenyl]sulfonyl}octahydro-1H-2,1-benzothiazine 2,2-dioxide

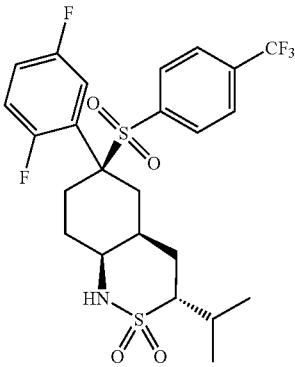

Step 1

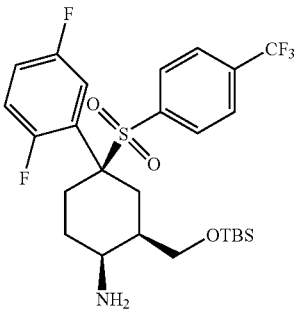

The product from Example 1 Step 2 was treated with boron trifluoride etherate as described in Example 1 Step 5. The resulting alcohol (2 g, 3.1 mmol) in dichloromethane (25 mL) was treated with triethylamine (1.7 mL, 12.4 mmol), 4-dimethylaminopyridine (cat.) and ′butyldimethylsilyl chloride (1.16 g, 7.75 mmol). After 16 hours the mixture was washed with 10% citric acid (10 mL), sodium bicarbonate (sat., 20 mL) and brine (sat. 15 mL). The organics were dried (MgSO$_4$) and evaporated and the residue was filtered through silica eluting with 1% ammonia in ethyl acetate to give the desired t-butyldimethylsilyl ether as a white solid (1.8 g) MS ES+564.

Step 2

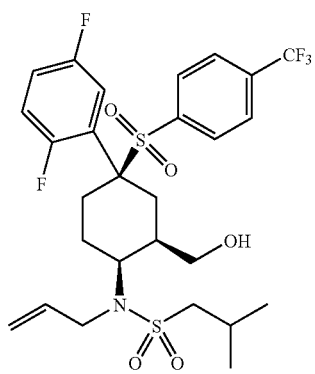

The silyl ether from Step 1 (1.8 g, 3.2 mmol) and isobutanesulfonyl chloride (1.12 g, 8 mmol) were stirred in dichloromethane (20 mL) and triethylamine (1.34 mL, 9.5 mmol) was added. After stirring at room temperature for 16 h., the mixture was evaporated to dryness and the residue was partitioned between ethyl acetate and 2 M hydrochloric acid. The organic layer was collected, washed with 2 M hydrochloric acid and then 4 M sodium hydroxide, dried (MgSO$_4$), filtered and the solvent removed in vacuo. The residue was purified by column chromatography (eluting with 20% ethyl acetate in hexanes) to give the sulfonamide (900 mg). This product was dissolved in dimethylformamide (6 mL) and sodium hydride (60% dispersion in mineral oil, 132 mg, 3.3 mmol) was added. The mixture was stirred at room temperature for 30 min., allyl bromide (1.1 mL, 13 mmol) was added, then the mixture was heated to 65° C. over 72 hrs. After cooling to room temperature and quenching with water, the mixture was extracted with ethyl acetate. The organic extract was washed with water, dried (MgSO$_4$), filtered and the solvent was removed. The residue was purified by column chromatography on silica gel eluting with 20% ethyl acetate: 80% isohexane to give the N-allyl derivative (400 mg). $^1$H NMR (360 MHz, CDCl$_3$) δ 7.67 (2H, d, J 8.3 Hz), 7.52 (2H, d, J 8.3 Hz), 7.10-7.05 (2H, m), 6.85-6.79 (1H, m), 5.96-5.91 (1H, m), 5.45 (1H, d, J 17.3 Hz), 5.34 (1H, d, J 10.4 Hz), 4.22-4.09 (1H, m), 4.01-3.98 (1H, m), 3.86-3.81 (1H, m), 3.51-3.40 (2H, m), 2.88-2.63 (4H, m), 2.49-2.43 (1H, m), 2.32-2.24 (2H, m), 2.09-2.04 (1H, m), 1.95-1.72 (2H, m) and 1.11-1.03 (6H, m).

Step 3

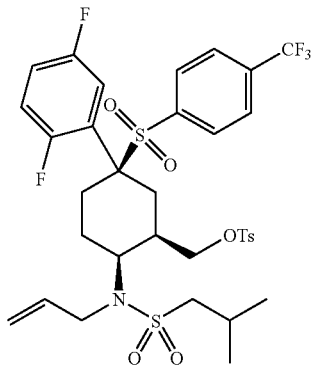

Prepared from the product of Step 2 (0.2 g) and p-toluenesulfonyl chloride (3 equiv.) in pyridine in the presence of 4-dimethylaminopyridine (0.3 equiv.) at 40° C. After extractive work-up, purification by column chromatography on silica, eluting with 30% ethyl acetate in hexanes gave the tosylate (185 mg).

Step 4

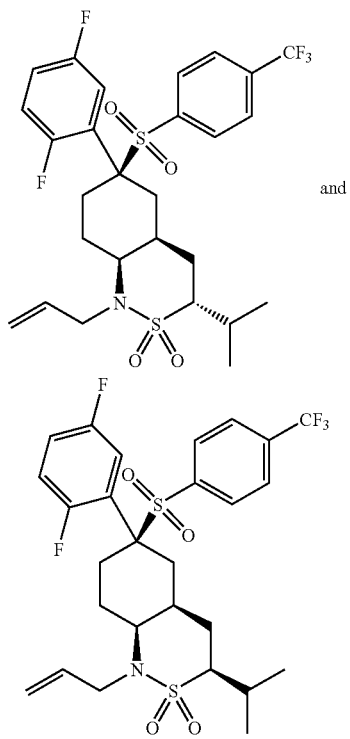

The tosylate from Step 3 (186 mg, 0.24 mmol) in tetrahydrofuran (9 mL) at −40° C. under nitrogen was treated with lithium hexamethyldisilazide (1.0 M solution in tetrahydrofuran, 480 μL) and the reaction mixture was allowed to warm up slowly to room temperature, then quenched with saturated aqueous ammonium chloride and extracted with ethyl acetate. The organic extract was washed with water, dried (MgSO$_4$), filtered and the solvent was removed. The residue was purified by column chromatography on silica gel eluting with 15% ethyl acetate: 85% iso-hexane. to give a less polar product as a white solid (48 mg):

$^1$H NMR (500 MHz, CDCl$_3$) δ 7.66 (2H, d, J 8 Hz), 7.52 (2H, d, J 8 Hz), 7.11-7.07 (1H, m), 6.93-6.75 (2H, m), 6.06-5.96 (1H, m), 5.29-5.22 (2H, m), 4.41-4.33 (1H, m), 3.69-3.48 (2H, m), 3.07-2.99 (1H, m), 2.89-2.72 (1H, m), 2.61-2.20 (5H, m), 1.90-1.73 (2H, m), 1.48-1.30 (2H, m), 1.17 (3H, d, J=7 Hz) and 1.05 (3H, d, J=7 Hz); and also a more polar product as a white solid. (67 mg):

$^1$H NMR (500 MHz, CDCl$_3$) δ7.65 (2H, d, J 8 Hz), 7.54 (2H, d, J 8 Hz), 7.07-7.03 (2H, m), 6.86-6.78 (1H, m), 5.75-5.65 (1H, m), 5.04-4.99 (2H, m), 3.95 (1H, dd, J=15.5 and 4.5 Hz), 3.63 (1H, dd, J=15.5 and 6.5 Hz), 3.29-3.24 (1H, m), 2.76-2.72 (1H, m), 2.61-2.52 (4H, m), 2.49-2.42 (1H, m), 2.40-2.18 (3H, m), 2.09-2.00 (1H, m), 1.75-1.68 (1H, m), 1.17 (3H, d, J=6.8 Hz) and 1.09 (3H, d, J=6.8 Hz).

Step 5

The less polar product from Step 4 (40 mg, 0.067 mmol) was treated as described in Example 1 Step 8 to give the title compound as a white solid. 23 mg. $^1$H NMR (500 MHz, CDCl$_3$) δ7.67 (2H, d, J 8.3 Hz), 7.53 (2H, d, J 8.0 Hz), 7.25-6.88 (2H, m), 7.11-7.06 (1H, m), 4.68-4.50 (1H, brs), 3.69-3.68 (1H, m), 3.00-2.96 (1H, m), 2.71-2.65 (1H, m), 2.60-2.27 (3H, m), 2.18-2.13 (1H, m), 2.02-1.87 (2H, m), 1.80-1.52 (3H, m), 1.22 (3H, d, J 6.9 Hz), 1.07 (3H, d, J 6.9 Hz). m/z (ES$^-$) (M−1) 550.

Example 5

(3SR,4aRS,6RS,8aSR)-6-(2,5-difluorophenyl)-3-isopropyl-6-{[4-(trifluoromethyl)phenyl]sulfonyl}octahydro-1H-2,1-benzothiazine 2,2-dioxide

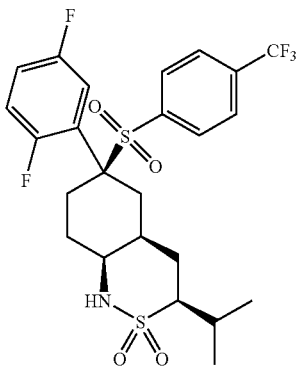

Step 5 of Example 4 was repeated, using the more polar isomer from Step 4 (40 mg, 0.067 mmol) to give the title compound as a white solid. (23 mg). $^1$H NMR (500 MHz, CDCl$_3$) δ7.68 (2H, d, J 8.3 Hz), 7.54 (2H, d, J 8.2 Hz), 7.10-7.06 (2H, m), 6.87-6.82 (1H, m), 4.47 (1H, d, J 8.9 Hz), 3.60-3.57 (1H, m), 2.82-2.77 (1H, m), 2.71-2.52 (2H, m), 2.40-2.20 (4H, m), 1.98 (1H, dd, J 15.1 and 2 Hz), 1.81-1.77 (2H, m), 1.76-1.74 (1H, m), 1.26 (3H, d, J 6.4 Hz), 1.11 (3H, d, J 6.8 Hz). m/z (ES$^-$) (M−1) 550.

Example 6

(3S,4aR,6R,8aS)-6-[(4-chlorophenyl)sulfonyl]-6-(2,5-difluorophenyl)-3-ethyloctahydro-1H-2,1-benzothiazine 2,2-dioxide

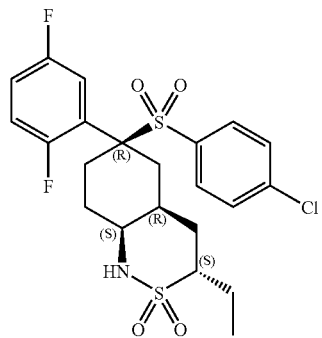

Step 1

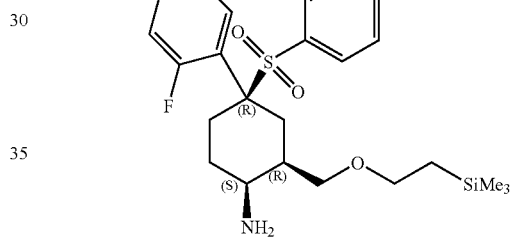

Intermediate 4 was treated as described in Example 1 Steps 1 and 2. The resulting product (80% e.e) (3.6 g, 6.96 mmol) was dissolved in iso-propanol (34 mL) and (1S)-(+)-camphor sulfonic acid (1.37 g, 5.91 mmol) was added. The mixture was heated to reflux, allowed to cool to room temperature slowly, and then left in the refrigerator overnight. The resulting solid was collected, washed with pre-cooled (~5° C.) isopropanol, then suspended in ethyl acetate and washed with 4M sodium hydroxide. The organics were dried (MgSO$_4$), filtered and the solvent removed to give the chiral amine (98% e.e). Yield 3 g, $^1$H NMR CDCl$_3$ 7.39-7.31 (4H, m), 7.09-6.96 (2H, m), 6.85-6.80 (1H, m), 3.48-3.15 (5H, m), 2.93-2.29 (4H, m), 1.74-1.19 (3H, m), 0.93-0.89 (2H, m) and 0.03 (9H, s).

MS MH+ 516(518).

Step 2

The amine from Step 1 (3 g) was elaborated as described for Example 1 Steps 3-8 to provide the desired homochiral sulfonamide (60 mg).

$^1$H NMR (500 MHz, CD$_3$OH) δ 77.51 (2H, d, J 8.7 Hz), 7.40 (2H, d, J 7.9 Hz), 7.25-7.11 (2H, m), 7.04-6.94 (1H, m), 3.55-3.51 (1H, m), 3.03-2.97 (1H, m), 2.75-2.32 (4H, m), 2.17-2.07 (1H, m), 2.01-1.93 (2H, m), 1.91-1.84 (1H, m), 1.75-1.57 (2H, m), 1.50-1.44 (1H, m) and 1.11 (3H, t, J 7.6 Hz).

Example 7

(3S,4aR,6R,8aS)-6-(2,5-difluorophenyl)-3-ethyl-6-{[4-(trifluoromethyl)phenyl]sulfonyl}octahydro-1H-2,1-benzothiazine 2,2-dioxide

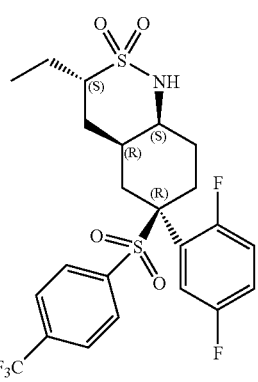

alternative route.

Step 1

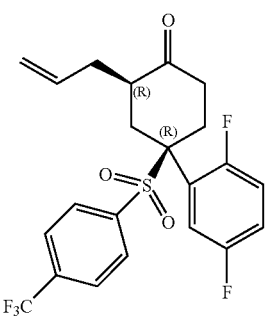

A solution of (1S)-1-phenyl-N-[(1S)-1-phenylethyl]ethanamine (10.8 g, 47.85 mmol) and oven-dried lithium chloride (3.0 g, 71.80 mmol) in tetrahydrofuran (200 ml) was degassed under nitrogen. The reaction mixture was cooled to −78° C. (internal temperature) and treated with n-butyl lithium (1.6M in hexane, 30 ml, 47.85 mmol), dropwise over 25 minutes. After the addition, the reaction was warmed to −20° C. and then cooled to −100° C. and stirred for 2 hours. A solution of 4-(2,5-difluorophenyl)-4-[[4-(trifluoromethyl) phenyl]sulfonyl]-cyclohexanone (20 g, 47.85 mmol) in tetrahydrofuran (100 ml) (cooled to −78° C.) was cannulated into the reaction vessel over 20 minutes. After a further 30 minutes at −100° C., allyl iodide (8.80 ml, 95.60 mmol) was added and the reaction mixture was allowed to warm to room temperature over 18 hours. The reaction mixture was acidified with citric acid solution (200 ml) and diluted with ethyl acetate (300 ml). The ethyl acetate layer was separated and re-washed with citric acid solution (200 ml), 10% ammonia solution (200 ml), brine, dried over MgSO$_4$, filtered and evaporated in vacuo. Purification by column chromatography gave the title compound as a white solid (8.97 g, 41%, 70% ee).

A solution of this material (73.1 g, 61% ee) in toluene (181 ml) was added dropwise to isohexane (760 ml) stirring at 70° C., over 45 minutes. The reaction mixture was seeded with racemic product (100 mg) and was cooled slowly over 2½ hours. The resultant solid was filtered and the filtrate was evaporated in vacuo resulting in clear gummy oil (49 g, 95% ee).

Step 2

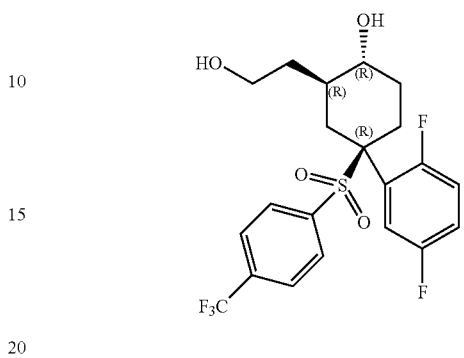

Oxygen was bubbled through a stirred solution of the product of Step 1 (67.8 g, 148 mmol) in dichloromethane (750 ml) and methanol (150 ml) at −78° C. for 10 minutes. Ozone was bubbled into the reaction mixture until a blue coloration persisted (3½ hours), followed by oxygen and then nitrogen until the blue color disappeared. Sodium borohydride (14 g, 370 mmol) was added to the reaction mixture, which was then allowed to warm to room temperature slowly. The mixture was acidified with citric acid solution (200 ml) and 2N hydrochloric acid, until pH 2, and diluted with dichloromethane (800 ml). The dichloromethane layer was separated and washed with water, brine, dried over MgSO$_4$, filtered and evaporated in vacuo. Purification by recrystallization from ether and isohexane (50:50), gave the diol as a white solid (50 g, 73%, 97% ee).

Step 3

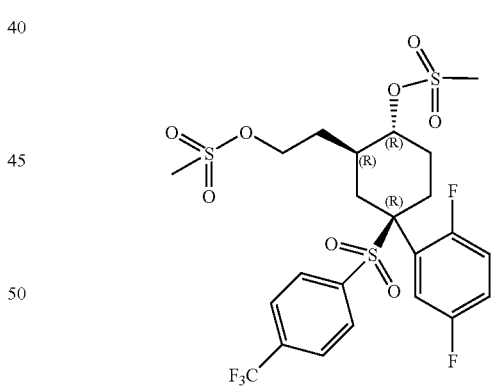

Methanesulfonyl chloride (20 ml, 259 mmol) was added slowly to a solution of the product of Step 2 (50 g, 108 mmol) in dichloromethane (700 ml) and triethylamine (45 ml, 324 mmol), stirring at −10° C. The reaction mixture was allowed to stir at −10° C. for 2 hours. The reaction was acidified with citric acid solution (500 ml) and diluted with dichloromethane (500 ml). The dichloromethane layer was separated and washed with sodium hydrogen carbonate solution (500 ml), brine, dried over MgSO$_4$, filtered and evaporated in vacuo to give the bis-mesylate as white foam (67.7 g, >100%), which was used without further purification.

Step 4

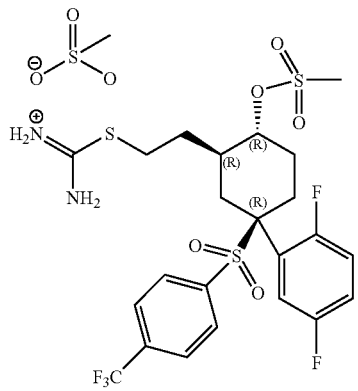

A solution of the product of Step 3 (67.7 g, 109 mmol) in ethanol was treated with thiourea (8.7 g, 115 mmol). The reaction mixture was stirred at 80° C. for 18 hours, cooled to room temperature and evaporated in vacuo to give the desired product as pale yellow foam (80.6 g, >100%).

Step 5

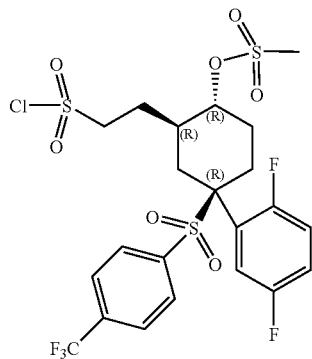

Acetic acid (500 ml) was added to a solution of the product of Step 4 (80.7 g) in water (100 ml) at room temperature. Chlorine gas (approximately 55 g) was bubbled through the reaction mixture for 30 minutes, until the reaction mixture turned a dark yellow. The reaction mixture was diluted with diethyl ether (1000 ml) and water (1000 ml). The ether layer was separated and washed with a further portion of water (1000 ml), sodium sulfite solution (500 ml), sodium hydrogen carbonate solution (3×500 ml), brine, dried over MgSO$_4$, filtered and evaporated in vacuo to give the sulfonyl chloride as a white foam 65.7 g (>100%).

Step 6

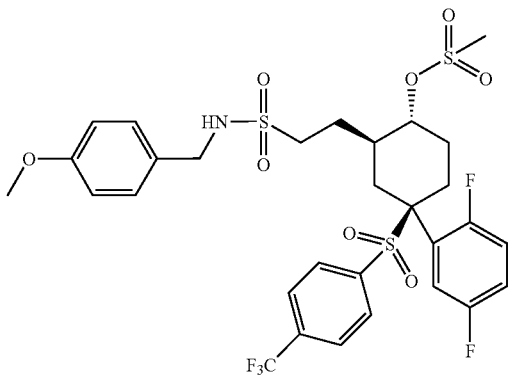

4-Methoxybenzylamine (35 ml, 263 mmol) was added dropwise over 10 minutes to a solution of the product of Step 5 (65.7 g, 105 mmol in dichloromethane (500 ml) stirred at 0° C., under nitrogen. The reaction mixture was warmed to room temperature over 90 minutes, diluted with dichloromethane (500 ml) and acidified with citric acid solution (500 ml). The dichloromethane layer was separated and washed with brine, water (700 ml), dried over MgSO$_4$, filtered and evaporated in vacuo. Purification by column chromatography gave the title intermediate as a pale brown foam (59.3 g, 88% over 4 steps).

Step 7

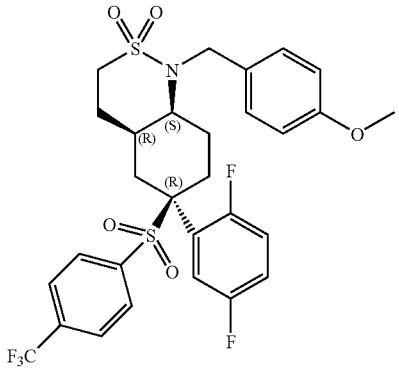

Sodium hydride (4.90 g, 127 mmol) was added to a solution of the product of Step 6 (59.3 g, 82 mmol) dissolved in dimethylformamide (700 ml). After stirring at room temperature for 10 minutes the reaction mixture was heated to 75° C. After 2 hours the reaction mixture was cooled to room temperature, acidified with citric acid solution (500 ml) and diluted with ethyl acetate (800 ml). The ethyl acetate layer was separated, washed with water (3×500 ml), brine, dried over MgSO$_4$, filtered and evaporated in vacuo. Purification by column chromatography gave the cyclised intermediate as white solid (28.7 g, 56%).

Step 8

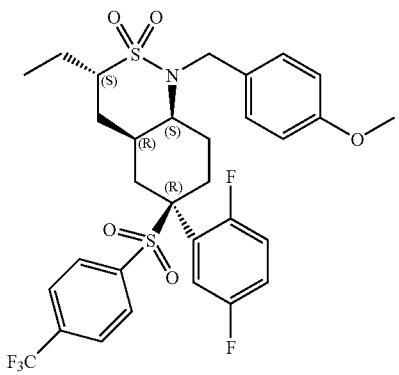

Lithium bis(trimethylsilyl)amide (1M in THF, 114 ml, 114 mmol) was added dropwise to a solution the product of Step 7 (28.7 g, 45.5 mmol) in tetrahydrofuran (300 ml) stirring at −2° C. (internal temperature). The reaction mixture was stirred for 1 hour at 0° C. under nitrogen, then cooled to −78° C. and treated with ethyl iodide (4.7 ml, 59.2 mmol). The reaction mixture was stirred at −25° C. for 18 hours then warmed to −8° C. and then to room temperature over 2 hours. The reaction was diluted with ethyl acetate (500 ml), water (500 ml) and acidified with citric acid solution (500 ml). The ethyl acetate layer separated and the aqueous layer was extracted with ethyl acetate (3×500 ml). The organics combined, washed with brine, dried over MgSO$_4$, filtered and evaporated in vacuo. Purification by column chromatography gave the alkylated intermediate as a white foam (23.1 g, 77%).

Step 9:

(3S,4aR,6R,8aS)-6-(2,5-difluorophenyl)-3-ethyl-6-{[4-(trifluoromethyl)phenyl]sulfonyl}octahydro-1H-2,1-benzothiazine 2,2-dioxide

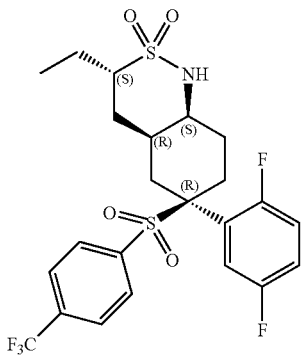

A solution of the product of Step 8 (23.1 g) in dichloromethane (115 ml) was treated with trifluoroacetic acid (60 ml) dropwise over 5 minutes, and stirred at room temperature under nitrogen for 30 minutes. The reaction mixture was evaporated in vacuo and purified by column chromatography gave the title product as white foam (17 g, 90%, 98.5% ee).

The white foam (17 g, 98.5% ee) was dissolved in ethyl acetate (34 ml) and heated to 70° C. Heptane (136 ml) was added portionwise to the stirred solution under nitrogen. After 2 hours the reaction solution was seeded with a homochiral sample of the title compound and allowed to stir for a further 1 hour and then cooled to room temperature. The resulting white solid was collected by filtration (12 g, 99.5% ee).

$^1$H NMR δ (ppm)(CDCl$_3$): 7.67 (2H, d, J=8.3 Hz), 7.56 (2H, s), 7.11-7.07 (1H, m), 6.98-6.83 (2H, m), 4.71-4.58 (1H, m), 3.68 (1H, s), 3.12 (1H, q, J=9.8 Hz), 2.73 (1H, t, J=13.5 Hz), 2.54-2.40 (3H, m), 2.17-1.91 (4H, m), 1.65-1.48 (3H, m), 1.14 (3H, t, J=7.5 Hz).

What is claimed is:

1. A compound of formula I:

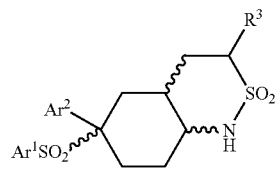

wherein the bonds indicated by wavy lines are mutually cis with respect to the cyclohexane ring;

R$^3$ represents H or a hydrocarbon group of up to 10 carbon atoms, optionally substituted with CF$_3$, CHF$_2$, halogen, CN, OR$^5$, COR$^5$, CO$_2$R$^5$, OCOR$^6$, N(R$^5$)$_2$, CON(R$^5$)$_2$ or NR$^5$COR$^6$;

R$^5$ represents H or C$_{1-4}$alkyl;

R$^6$ represents C$_{1-4}$alkyl; and

Ar$^1$ and Ar$^2$ independently represent phenyl or heteroaryl, either of which bears 0-3 substituents independently selected from halogen, CN, NO$_2$, CF$_3$, CHF$_2$, OH, OCF$_3$, CHO, CH=NOH, C$_{1-4}$alkoxy, C$_{1-4}$alkoxycarbonyl, C$_{2-6}$acyl, C$_{2-6}$alkenyl and C$_{1-4}$alkyl which optionally bears a substituent selected from halogen, CN, NO$_2$, CF$_3$, OH and C$_{1-4}$alkoxy;

or a pharmaceutically acceptable salt thereof.

2. A compound according to claim 1 wherein Ar$^1$ is selected from 6-(trifluoromethyl)-3-pyridyl and phenyl which is optionally substituted in the 4-position with halogen, CN, vinyl, allyl, acetyl, methyl or mono-, di- or trifluoromethyl;

and Ar$^2$ is selected from phenyl groups bearing halogen substituents in the 2- and 5-positions, the 2- and 6-positions, or in the 2-, 3- and 6-positions.

3. A compound according to claim 2 wherein Ar$^1$ is 4-chlorophenyl or 4-trifluoromethylphenyl and Ar$^2$ is 2,5-difluorophenyl.

4. A compound according to any previous claim wherein R$^3$ represents H or a non-aromatic hydrocarbon group of up to 6 carbon atoms which is unsubstituted.

5. A compound according to claim 4 wherein R$^3$ represents H, methyl, ethyl, n-propyl, isopropyl or allyl.

6. A compound according to claim 5 selected from (4aRS,6RS,8aSR)-6-(2,5-difluorophenyl)-6-{[4-(trifluoromethyl)phenyl]sulfonyl}octahydro-1H-2,1-benzothiazine 2,2-dioxide;

(3S,4aR,6R,8aS)-6-(2,5-difluorophenyl)-3-ethyl-6-{[4-(trifluoromethyl)phenyl]sulfonyl}octahydro-1H-2,1-benzothiazine 2,2-dioxide;

(3R,4aR,6R,8aS)-6-(2,5-difluorophenyl)-3-ethyl-6-{[4-(trifluoromethyl)phenyl]sulfonyl}octahydro-1H-2,1-benzothiazine 2,2-dioxide;

(3RS,4aRS,6RS,8aSR)-6-(2,5-difluorophenyl)-3-isopropyl-6-{[4-(trifluoromethyl)phenyl] sulfonyl}octahydro-1H-2,1-benzothiazine 2,2-dioxide;

(3SR,4aRS,6RS,8aSR)-6-(2,5-difluorophenyl)-3-isopropyl-6-{[4-(trifluoromethyl)phenyl] sulfonyl}octahydro-1H-2,1-benzothiazine 2,2-dioxide; and (3S,4aR,6R,8aS)-6-[(4-chlorophenyl)sulfonyl]-6-(2,5-difluorophenyl)-3-ethyloctahydro-1H-2,1-benzothiazine 2,2-dioxide;

and the pharmaceutically acceptable salts thereof.

7. A pharmaceutical composition comprising a compound according to any previous claim and a pharmaceutically acceptable carrier.

8. A process for preparing a compound of formula I as defined in claim 1 comprising the steps of:

(a) cyclising a compound of formula (2):

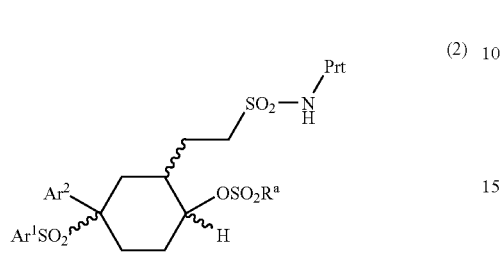

(2)

by treatment with strong base in an aprotic solvent to form a compound of formula (1):

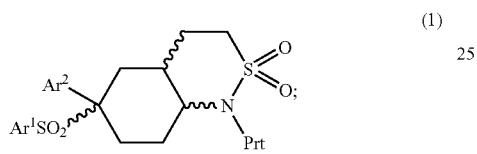

(1)

(b) optionally alkylating the compound of formula (1) with $R^{3a}$—L; and (c) removing the N-protecting group;

where Prt is a protecting group, L is a leaving group, $R^{3a}$ is $R^3$ that is other than H, $R^a$ is $C_{1-6}$alkyl which optionally bears up to 3 halogen substituents, or phenyl which optionally bears up to 3 substituents selected from halogen and $C_{1-4}$alkyl, and $Ar^1$, $Ar^2$ and $R^3$ are as defined in claim 1.

9. A compound of claim 1 or a pharmaceutically acceptable salt thereof wherein $Ar^1$ represents 4-trifluoromethylphenyl, $Ar^2$ represents 2,5-difluorophenyl, and $R^3$ represents ethyl.

10. A compound of claim 1 which is in the homochiral form of formula (IA)

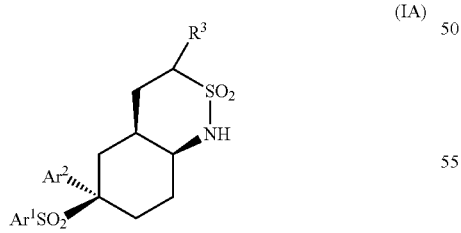

(IA)

or a pharmaceutically acceptable salt thereof.

11. A compound of claim 1 which is in the homochiral form of formula (IB)

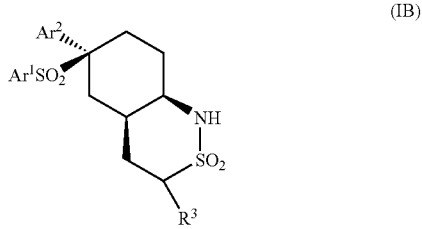

(IB)

or a pharmaceutically acceptable salt thereof.

12. A compound of claim 9 which is in the homochiral form of formula (IA)

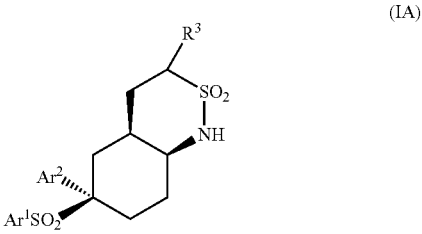

(IA)

or a pharmaceutically acceptable salt thereof.

13. A compound of claim 10 which is in the homochiral form of formula (IB)

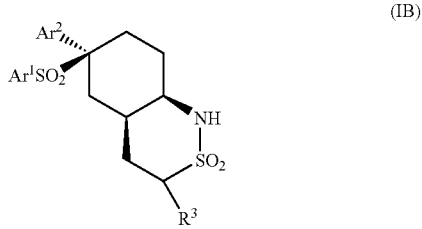

(IB)

or a pharmaceutically acceptable salt thereof.

* * * * *

UNITED STATES PATENT AND TRADEMARK OFFICE
CERTIFICATE OF CORRECTION

PATENT NO. : 7,342,009 B2  Page 1 of 1
APPLICATION NO. : 10/845833
DATED : March 11, 2008
INVENTOR(S) : Kevin Dinnell et al.

It is certified that error appears in the above-identified patent and that said Letters Patent is hereby corrected as shown below:

<u>Title page</u>,
Change Item (73) Assignee from "Merck & Co., Inc., Rahway, NJ (US)" to
--Merck Sharp & Dohme, Ltd., Hoddesdon, Hertfordshire (GB)--

Signed and Sealed this

Thirtieth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,342,009 B2  Page 1 of 1
APPLICATION NO. : 10/845833
DATED : March 11, 2008
INVENTOR(S) : Kevin Dinnell et al.

It is certified that error appears in the above-identified patent and that said Letters Patent is hereby corrected as shown below:

Column 30, line 40, the text reading "claim 10" should read --claim 9--.

Signed and Sealed this

Seventeenth Day of November, 2009

David J. Kappos
*Director of the United States Patent and Trademark Office*